United States Patent
Chihiro et al.

(10) Patent No.: US 6,291,487 B1
(45) Date of Patent: Sep. 18, 2001

(54) AGENT FOR INHIBITION OF CYTOKINE PRODUCTION AND AGENT FOR INHIBITION OF CELL ADHESION

(75) Inventors: Masatoshi Chihiro, Naruto; Takayuki Matsuzaki, Tokushima; Hisashi Nagamoto, Suita; Goro Miyakoda, Itano-gun, all of (JP); Shinobu Sueyoshi, Belmont, CA (US); Toyoki Mori; Kazuyoshi Kitano, both of Naruto (JP); Isao Takemura, Tokyo (JP); Hiroshi Yamashita, Itano-gun (JP); Muneaki Kurimura, Naruto (JP); Fujio Tabusa, Itano-gun (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/269,481
(22) PCT Filed: Sep. 29, 1997
(86) PCT No.: PCT/JP97/03466
§ 371 Date: Mar. 29, 1999
§ 102(e) Date: Mar. 29, 1999
(87) PCT Pub. No.: WO98/14191
PCT Pub. Date: Apr. 9, 1998

(30) Foreign Application Priority Data

Sep. 30, 1996 (JP) .................................... 8-258533

(51) Int. Cl.$^7$ .............................................. A61K 31/4436
(52) U.S. Cl. ....................................... 514/342; 546/270.4
(58) Field of Search ............................................. 514/342

(56) References Cited

FOREIGN PATENT DOCUMENTS 0 310 370   4/1989   (EP) .
0 513 387   11/1992  (EP) .

OTHER PUBLICATIONS

CA 120:29060, Rathjen et al, 1994.*
M. Chihiro et al., "Novel Thiazole Derivatives as Inhibitors of Superoxide Production by Human Neutrophils: Synthesis and Structure–Activity Relationship", J. Med. Chem., vol. 38, pp. 353–358, 1995.

JP 55 133366, "4–Alpha carboxy phenyl–2–thiazole derivs.–have excellent antiphlogistic, blood platelet aggregation inhibiting, anti thrombosis and antiinflammatory action", Derwent Publications Ltd., London, (Abstract Only), Oct. 17, 1980.

JP 05 112564, "Antiinflammatory phenyl:thiazole derivs.–prepd e.g. by ring cyclisation of beta–keto nitrile deriv. with hydroxylamine hydrochloride to give corresp. isoxazole", Derwent Publications Ltd. London, (Abstract Only), May 7, 1993.

* cited by examiner

*Primary Examiner*—Jane Fan
(74) *Attorney, Agent, or Firm*—Finnegan, Henderson, Farabow, Garrett & Dunner, L.L.P.

(57) ABSTRACT

The present invention provides an agent for inhibiting cytokine production or cell adhesion, comprising at least one compound selected from the group consisting of thiazole derivatives represented by the following general formula:

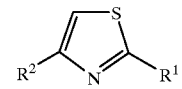

[wherein $R^1$ is a phenyl group which may have a lower alkoxy group(s) as a substituent(s) on the phenyl ring, and $R^2$ is a group represented by the following general formula:

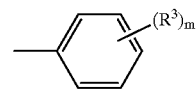

[wherein $R^3$'s, which may be the same or different, are each a carboxyl group, a lower alkoxy group or the like) or the like] and salts thereof.

12 Claims, No Drawings

AGENT FOR INHIBITION OF CYTOKINE PRODUCTION AND AGENT FOR INHIBITION OF CELL ADHESION

This is a 371 of PCT/JP97/03466 Sep. 29, 1997 now WO98/14191.

TECHNICAL FIELD

The present invention relates to an agent for inhibition of cytokine production and an agent for inhibition of cell adhesion.

BACKGROUND ART

A number of cytokines were discovered as protein factors which inhibit the expression of human physiological activities such as immune response, inflammation, hematopoiesis and the like, and their structures and functions have gradually been made clear. As a result, it is being clarified that the cytokines affect not only human immunological system but also various other human physiological activities and further have a close connection with the development, differentiation, homeostatis and diseases of human body.

Many cytokines such as TNF-α, IL-1β, IL-6, IFN-γ and the like are identified. It is known that they also have various pharmacological activities.

Of the above cytokines, TNF-α (Tumor necrosis factor-α) was discovered as an antineoplastic cytokine and was expected to be used as an anticancer agent. However, TNF-α was later found to be the same substance as cachectin (a cachexia inducer) and is reported to have, for example, a stimulating activity for production of IL-1 and other cytokines, an activity of proliferation of fibroblast, an endotoxin shock-inducing activity, an activity for increasing ICAM-1, ICAM-2 (intercellular adhesion molecules), ELAM (endothelial leukocyte adhesion molecule-1), etc. (these molecules are proteins for adhering leukocytes to endothelial cells) to accelerate the adhesion of leukocytes to endothelial cells, and an arthritis-causing activity such as bone resorption, cartilage destruction or the like [Beutler, B., et al., Nature, 316, 552–554 (1985); Peetre, C., et al., J. Clin. Invest., 78, 1694–1700 (1986); Kurt-Jones, E. A., et al., J. Immunol., 139, 2317–2324 (1987); Bevilacqua, M. P., et al., Science, 241, 1160–1165 (1989); Akatu, K. & Suda, T., Medical Practice, 8 (9) 1393–1396 (1991)].

It is also reported that the concentration of TNF in blood or neurolymph increases in infectious diseases by bacteria or parasites [Mitsuyama, M., Journal of Clinical and Experimental Medicine (IGAKU NO AYUMI), 159 (8) 467–470 (1991); Nakao, M., Journal of Clinical and Experimental Medicine (IGAKU NO AYUMI), 159 (8) 471–474 (1991)].

It is also reported that the activity of TNF is found in synovial fluid or serum, in chronic rheumatoid arthritis and that the activity is a TNF-α activity [Saxne, T., et al., Arthritis Rheum., 31, 1041 (1988); Chu, C. Q., et al., Arthritis Rheum., 34, 1125–1132 (1991); Macnaul, K. L., et al., J. Immunol., 145, 4154–4166 (1990); Brennan, F. M., et al., J. Immunol., 22, 1907–1912 (1992); Brennan, F. M., et al., Bri. J. Rheum., 31, 293–298 (1992)].

It is also reported that the concentration of TNF is high in the sputa of patients of ARDS (acute respiratory distress syndrome) which is a serious respiratory disease [Millar, A. B., et al., Nature, 324, 73 (1986)] and that TNF is associated with viral fulminant hepatitis [Muto, Y., et al., Lancet, ii, 72–74 (1986)].

It is also reported that the concentration of TNF-α in blood is high in myocardial ischemia such as acute myocardial infarction [Latini, R., et al., J. Cardiovasc. Pharmacol., 23, 1–6 (1994)]. It is suggested that TNF-α is associated with such a disease [Lefer, A. M., et al., Science, 249, 61–64 (1990)]. It has recently been reported that TNF-α suppresses myocardial contractility [Finkel, M. S., et al., Science, 257, 387–389 (1992); Pagani, D. F., et al., J. Clin. Invest., 90, 389–398 (1992)].

Currently, no satisfactory chemotherapy is developed yet for the above-mentioned various diseases such as chronic rheumatoid arthritis, endotoxin shock, ARDS and the like. To these diseases are merely applied, in a symptomatic treatment, steroidal agents, anti-inflammatory agents, agents for inhibition of platelet agglutination, antibiotics, etc. As it was suggested as mentioned above that there is a close connection between the above diseases and the rise in concentration or activity of TNF-α, it has recently been tried to apply TNF-α antibody or the like to the diseases; however, such an approach has given no satisfactory result, either. Therefore, it is desired in the art to develop a drug for treatment of the above diseases, which can suppress the excessive production of, in particular, TNF-α, according to a novel mechanism.

B cells are activated by antigen, proliferated and differentiated into antibody-producing cells. IL-6 is known to be a cytokine participating in this differentiation.

It is clear that IL-6 not only plays an important role in antibody production of B cells, but also induces the proliferation and differentiation of T cells. It is also clear that IL-6 acts on liver cells to induce the synthesis of proteins in acute phase, acts on hemopoietic cells to promote the formation of pluripotential colonies, and is an important factor in biophylactic systems such as immune system, hemopoietic system, nerve system, liver and the like.

As the diseases with which IL-6 is associated, there are mentioned a series of autoimmune diseases such as hyper-γ-globulinemia, chronic rheumatoid arthritis, systemic lupus erythematosus (SLE) and the like; monoclonal B cell abnormal disease (e.g. myeloma); polyclonal B cell abnormal disease; atrial myxoma; Castleman syndrome; primary glomerulonephritis; mesangial proliferative nephritis; cancerous cachexia; Lennander's lymphoma; psoriasis; Kaposi's sarcoma appearing in AIDS; postmenopausal osteoporosis; and so forth.

IL-1β is known to have various physiological activities. Specific examples of these activities are inhibition of tumor cell, increase of cytokine production from activated T cells, proliferation of fibroblast, synoviocyte and vessel endothelium, catabolism and thermacogenesis of cell, differentiation of activated B cell, increase of NK activity, adhesion of neutrophils, anti-inflammation, inhibition of radiation disorder, etc.

When IL-1β is produced at an increased rate and becomes excessive, IL-1β is thought to give rise to various diseases such as chronic rheumatoid arthritis, chronic inflammatory diseases and the like.

IFN is known to have various physiological activities and is actually detected in tissues and blood during many diseases. The diseases whose onset is considered to have a close connection with IFN, include viral infectious diseases, infectious diseases by microorganisms other than viruses, chronic rheumatoid arthritis, collagen diseases (e.g. SLE), I-type allergy, uveitis, Behcet's disease, sarcoidosis, arteriosclerosis, diabetes, fulminant hepatitis, malignant tumor, Kawasaki disease, wounds of skin or mucosa, etc. [Journal of Clinical and Experimental Medicine (IGAKU NO AYUMI), 174 (14), p. 1077, 1995].

Neutrophils express a bactericidal action to the enemy incoming into human body, by migration, phagocytosis, production of reactive oxygen and release of lysosomal enzymes. However, neutrophils are known to adhere to vascular endothelial cells and further infiltrate into tissues during the ischemia or reperfusion, or acute inflammation of various tissues, leading to tissue disorder.

As stated above, various cytokines are known to cause various diseases when the cytokines become excessive owing to, for example, the abnormally high production thereof. Therefore, it is desired to ameliorate the abnormal state of cytokine to prevent or treat various diseases.

It is also desired to develop an agent for inhibiting the tissue disorder caused by adhesion of neutrophils to vascular endothelial cells.

Some of the thiazole derivatives represented by the following general formula (1):

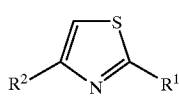

(1)

{wherein $R^1$ is a phenyl group which may have a lower alkoxy group(s) as a substituent(s) on the phenyl ring; and $R^2$ is a group represented by the following general formula:

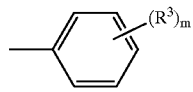

[wherein $R^3$'s, which may be the same or different, are each a carboxyl group, a lower alkoxy group, a lower alkyl group, a lower alkenyl group, a group represented by —(A)$_l$—NR$^4$R$^5$ (A is a lower alkylene group; $R^4$ and $R^5$, which may be the same or different, are each a hydrogen atom or a lower alkyl group; and l is 0 or 1), a hydroxyl group-substituted lower alkyl group, a lower alkoxy group-substituted lower alkoxy group, a lower alkoxy group-substituted lower alkoxycarbonyl group or a carboxyl group-substituted lower alkoxy group; and m is an integer of 1–3], or a heterocyclic ring residue having 1–2 hetero atoms selected from the group consisting of nitrogen atom, oxygen atom and sulfur atom, which heterocyclic ring residue may have, as a substituent(s) on the heterocyclic ring, 1–3 groups selected from the group consisting of carboxyl group and lower alkoxy group} and salts thereof, are known in, for example, JP-A-5-51318 and JP-A-6-65222. These thiazole derivatives and salts thereof are also well-known to be useful as a reactive oxygen inhibitor.

DISCLOSURE OF THE INVENTION

The object of the present invention is to provide an agent for inhibiting the abnormally high production of cytokines or adhesion of neutrophils to vascular endothelial cells, which satisfies the requirements of the art, i.e. an agent for inhibiting cytokine production or an agent for inhibiting cell adhesion.

The present inventor made a further study on the pharmacological actions of the thiazole derivatives represented by the above general formula (1) and salts thereof. As a result, the present inventor found out that these thiazole derivatives and salts thereof can act as an agent for inhibiting cytokine production or an agent for inhibiting cell adhesion, both satisfying the above object of the present invention. The present invention has been completed based on the finding.

According to the present invention, there is provided an agent for inhibiting cytokine production, comprising, as the active ingredient, at least one compound selected from the group consisting of thiazole derivatives represented by the above general formula (1) and salts thereof.

According to the present invention, there is also provided an agent for inhibiting cell adhesion, comprising, as the active ingredient, at least one compound selected from the group consisting of thiazole derivatives represented by the above general formula (1) and salts thereof.

According to the present invention, there is also provided an agent for inhibiting TNF-α production, comprising, as the active ingredient, at least one compound selected from the group consisting of thiazole derivatives represented by the above general formula (1) and salts thereof. of the thiazole derivatives represented by the general formula (1), preferred is 6-[2-(3,4-diethoxyphenyl) thiazole-4-yl]pyridine-2-carboxylic acid.

As mentioned previously, some of the thiazole derivatives of the general formula (1) and salts thereof and production processes thereof are described in JP-A-5-51318 and JP-A-6-65222, and these thiazole derivatives are known to be useful as an agent for inhibiting reactive oxygen. Meanwhile, the inhibition of cytokine production or cell adhesion according to the present invention has no connection with the above-mentioned inhibition of reactive oxygen by thiazole derivatives and is unpredictable from the inhibition of reactive oxygen.

The agent for inhibiting cytokine production or cell adhesion according to the present invention is useful for various diseases associated with the abnormally high production of cytokines, particularly TNF-α, IL-1β, IL-6 and IFN-γ, or with increased adhesion. The present agent can be suitably used as a preventive or therapeutic agent articularly for chronic rheumatoid arthritis; endotoxin shock; ARDS caused by aspiration of gastric contents, toxic gas, sepsis, etc.; burn; asthma; myocardial infarction in myocardial ischemia; viral myocarditis in acute phase; chronic heart failure (e.g. idiopathetic dilated cardiomyopathy); etc. The present agent can also be suitably used as a preventive or therapeutic agent for ischemia-reperfusion injury caused at the time of coronary arterial bypass graft (CABG) or the use of artifical heart lung apparatus; shift from systemic inflammatory response syndrome (SIRS) toward organ failure (e.g. severe acute pancreatitis, disseminated intravasocular coagulation (DIC)); multiple organ failure caused by hepatic insufficiency after hepatectomy such as resection of hepatic cancer, or acute pancreatitis; severe acute pancreatitis; inflammatory bowel diseases such as ulcerative colitis, Crohn disease and the like; a series of autoimmune diseases such as hyper-γ-globulinemia, chronic rheumatoid arthritis, systemic lupus erythematosus (SLE), multiple sclerosis and the like; metastasis of cancer; rejection in transplantation; monoclonal B cell abnormal disease (e.g. myeloma); polyclonal B cell abnormal disease; atrial myxoma; Castleman syndrome; primary glomerulonephritis; mesangial proliferative glomerulonephritis; cancerous cachexia; Lennander's lymphoma; psoriasis; atopic dermatitis; Kaposi's sarcoma appearing in AIDS; postmenopausal osteoporosity; diabetes; sepsis; arteriosclerosis; and inflammatory diseases (e.g. angitis and hepatitis).

Listed below are literatures relating to the diseases for which the present agent for inhibition of cytokine production or for inhibition of cell adhesion is efficacious.

(1) Literatures relating to transplantation
  (a) Kojima, Y. et al., (1993) Cardiovasc. Surg., 1, 577–582
  (b) Yamataka, T. et al., (1993) J. Pediatr. Surg., 28, 1451–1457
  (c) Stepkowshi, S. M. et al., (1994) J. Immunol., 153, 5336–5346
(2) Literatures relating to asthma
  (a) Ohkawara, Y. et al., (1995) Am. J. Respir. Cell Mol. Biol., 12, 4–12
  (b) Chihara, J. et al., (1995) Immunol. Lett., 46, 241–244
  (c) Hakansson, L. et al., (1995) J. Allergy Clin. Immunol., 96, 941–950
(3) Literatures relating to arterioscrelosis
  (a) Poston, R. N. et al., (1992) Am. J. Pathol., 140, 665–673
  (b) Ross, P., (1993) Nature, 362, 801–809
  (c) Li, H. et al., (1993) Arterioscler. & Thromb., 13, 197–204
  (d) Walpola, P. L. et al., (1995) Arterioscler. Thromb. Vasc. Biol., 15, 2–10
(4) Literatures relating to metastasis of cancer
  (a) Garofalo, A. et al., (1995) Cancer Res., 55, 414–419
  (b) Gardner, M. J. et al., (1995) Cancer Lett., 91, 229–234
(5) Literatures relating to diabetes
  (a) McLeod, D. S. et al., (1995) Am. J. Pathol., 147, 642–653
  (b) Schmidt, A. M. et al., (1995) J. Clin. Invest., 96, 1395–1403
  (c) Jakubowski, A. et al., (1995) J. Immunol., 155, 938–946
(6) Literatures relating to multiple screlosis
  (a) Dore-Duffy, P. et al., (1993) Adv. Exp. Med. Biol., 331, 243–248
  (b) Mizobuchi, M. and Iwasaki, Y., (1994) Nippon Rinsho, 52, 2830–2836
  (c) Cannella, B. and Raine, C. S., (1995) Ann. Neurol., 37, 424–435
(7) Literatures relating to multiple organ failure
  (a) Law, M. M. et al., (1994) J. Trauma., 37, 100–109
  (b) Anderson, J. A. et al., (1996) J. Clin. Invest., 97, 1952–1959
(8) Literatures relating to atopic dermatitis
  (a) Meng, H. et al., (1995) J. Cell Physiol., 165, 40–53
  (b) Santamaria, L. F. et al., (1995) Int. Arch. Allergy Immunol., 107, 359–362
  (c) Wakita, H. et al., (1994) J. Cutan. Pathol., 21, 33–39
(9) Literatures relating to psoriasis
  (a) Groves, R. W. et al., (1993) J. Am. Acad. Dermatol., 29, 67–72
  (b) Uyemura K., (1993) J. Invest. Dermatol., 101, 701–705
  (c) Lee, M. L. et al., (1994) Australas J. Dermatol., 35, 65–70
  (d) Wakita, H. and Takigawa, M., (1994) Arch. Dermatol., 130, 457–463
(10) Literatures relating to chronic rheumatoid arthritis
  (a) Hale, P. L. et al., (1993) Arthritis Rheum., 32, 22–30
  (b) Iigo Y. et al., (1991) J. Immunol., 147, 4167–4171
(11) Literatures relating to acute respiratory distress syndrome
  (a) Tate, R. M. and Repine, J. E., (1983) Am. Rev. Respir. Dis., 128, 552–559
  (b) Beutler, B., Milsark, I. W. and Cerami, A. C., (1985) Science, 229, 869–871
  (c) Holman, R. G. and Maier, R. V., (1988) Arch. Surg., 123, 1491–1495
  (d) Windsor, A. et al., (1993) J. Clin. Invest., 91, 1459–1468
  (e) van der Poll, T. and Lowry, S. F., (1995) Prog. Surg. Basel. Karger, 20, 18–32
(12) Literatures relating to ischemic reperfusion injury
  (a) Yamazaki, T. et al., (1993) Am. J. Pathol., 143, 410–418
  (b) Vaage, J. and Valen, G., (1993) Acand. J. Thorac. Cardiovasc. Surg. Suppl., 41
  (c) McMillen, M. A. et al., (1993) Am. J. Surg., 166, 557–562
  (d) Bevilacqua, M. P. et al., (1994) Annu. Rev. Med., 45, 361–378
  (e) Panes, J. and Granger, D. N., (1994) Dig. Dis., 12, 232–241
(13) Literatures relating to inflammatory bowel disease
  (a) Mahida, Y. R. et al., (1989) Gut, 30, 835–838
  (b) Nakamura, S. et al., (1993) Lab. Invest., 69, 77–85
  (c) Beil, W. J. et al., (1995) J. Leukocyte Bio., 58, 284–298
  (d) Jones, S. C. et al., (1995) Gut, 36, 724–730
(14) Literatures relating to systemic inflammatory response syndrome
  (a) K. Mori and M. Ogawa, (1996) Molecular Medicine, 33, 9, 1080–1088
  (b) Dinarello, C. A. et al., (1993) JAMA, 269, 1829

Specific examples of each of the groups used in the general formula (1) are as follows.

The phenyl group which may have a lower alkoxy group (s) as a substituent(s) on the phenyl ring, include phenyl groups which may have 1–3 straight chain or branched chain alkoxy groups of 1–6 carbon atoms as a substituent(s) on the phenyl ring, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3-propoxy-4-methoxyphenyl, 3,5-dimethoxyphenyl, 3,4-dipentyloxyphenyl, 3,4,5-trimethoxyphenyl, 3-methoxy-4-ethoxyphenyl and the like.

The lower alkyl group includes straight chain or branched chain alkyl groups of 1–6 carbon atoms, such as methyl, ethyl, propyl, isopropyl, butyl, tert-butyl, pentyl, hexyl and the like.

The lower alkoxy group includes straight chain or branched chain alkoxy groups of 1–6 carbon atoms, such as methoxy, ethoxy, propoxy, isopropoxy, butoxy, tert-butoxy, pentyloxy, hexyloxy and the like.

The lower alkenyl group includes straight chain or branched chain alkenyl groups of 2–6 carbon atoms, such as vinyl, allyl, 2-butenyl, 3-butenyl, 1-methylallyl, 2-pentenyl, 2-hexenyl and the like.

The group represented by —(A)$_l$—NR$^4$R$^5$ (A is a lower alkylene group; R$^4$ and R$^5$, which may be the same or different, are each a hydrogen atom or a lower alkyl group; and l is 0 or 1) includes groups represented by —(A)$_l$—NR$^4$R$^5$ (A is an alkylene group of 1–6 carbon atoms; R$^4$ and R$^5$, which may be the same or different, are each a hydrogen atom or a straight chain or branched chain alkyl group of 1–6 carbon atoms; and l is 0 or 1), such as amino, methylamino, ethylamino, propylamino, isopropylamino, tert-butylamino, butylamino, pentylamino, hexylamino, dimethylamino, diethylamino, methylethylamino, methylpropylamino, aminomethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethyl, propylaminomethyl, butylaminomethyl, pentylaminomethyl, hexylaminomethyl, dimethylaminomethyl, 2-dimethylaminoethyl and the like.

The hydroxyl group-substituted lower alkyl group includes straight chain or branched chain alkyl groups of 1–6 carbon atoms having 1–3 hydroxyl groups, such as hydroxymethyl, 2-hydroxyethyl, 1-hydroxyethyl, 1,2-dihydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 1-hydroxyisopropyl,2-methyl-3-hydroxypropyl and the like.

The lower alkoxy group-substituted lower alkoxy group includes alkoxyalkoxy groups whose alkoxy moieties are each a straight chain or branched chain alkoxy group of 1–6 carbon atoms, such as methoxymethoxy, 3-methoxypropoxy, ethoxymethoxy, 4-ethoxybutoxy, 6-propoxyhexyloxy, 5-isopropoxypentyloxy, 1,1-dimethyl-2-butoxyethoxy, 2-methyl-3-tert-butoxypropoxy, 2-pentyloxyethoxy, hexyloxymethoxy and the like.

The lower alkoxycarbonyl group can be exemplified by straight chain or branched chain alkoxycarbonyl groups of 1–6 carbon atoms, such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like.

The lower alkoxy group-substituted lower alkoxycarbonyl group includes alkoxy group-substituted alkoxycarbonyl groups whose alkoxy moieties are each a straight chain or branched chain alkoxy group of 1–6 carbon atoms, such as methoxymethoxycarbonyl, 3-methoxypropoxycarbonyl, ethoxymethoxycarbonyl, 4-ethoxybutoxycarbonyl, 6-propoxyhexyloxycarbonyl, 5-isopropoxypentyloxycarbonyl, 1,1-dimethyl-2-butoxyethoxycarbonyl, 2-methyl-3-tert-butoxypropoxycarbonyl, 2-pentyloxyethoxycarbonyl, hexyloxymethoxycarbonyl and the like.

The carboxyl group-substituted lower alkoxy group includes carboxyl group-substituted alkoxy groups whose alkoxy moiety is a straight chain or branched chain alkoxy group of 1–6 carbon atoms, such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy and the like.

The heterocyclic ring residue having 1–2 hetero atoms selected from the group consisting of nitrogen atom, oxygen atom and sulfur atom includes, for example, pyrrolidinyl, piperidinyl, piperazinyl, morpholino, pyridyl, 1,2,5,6-tetrahydropyridyl, thienyl, quinolyl, 1,4-dihydroquinolyl, benzothiazolyl, pyrazinyl, pyrimidyl, pyridazinyl, pyrrolyl, carbostyril, 3,4-dihydrocarbostyril, 1,2,3,4-tetrahydroquinolyl, indolyl, isoindolyl, indolinyl, benzimidazolyl, benzoxazolyl, imidazolidinyl, isoquinolyl, quinazolinyl, quinoxalinyl, cinnolinyl, phthaladinyl, carbazolyl, acridinyl, chromanyl, isoindolinyl, isochromanyl, pyrazolyl, imidazolyl, pyrazolidinyl, phenothiazinyl, benzofuryl, 2,3-dihydro[b]furyl, benzothienyl, phenoxathienyl, phenoxazinyl, 4H-chromenyl, 1H-indazolyl, phenazinyl, xanthenyl, thianthrenyl, 2-imidazolinyl, 2-pyrrolinyl, furyl, oxazolyl, isooxazolyl, thiazolyl, isothiazolyl, pyranyl, 2-pyrazolinyl, quinuclidinyl, 1,4-benzoxazinyl, 3,4-dihydro-2H-1,4-benzoxazinyl, 3,4-dihydro-2H-1,4-benzthiazinyl, 1,4-benzthiazinyl, 1,2,3,4-tetrahydroquinoxalinyl, 1,3-dithia-2,4-dihydronaphthalenyl, phenanthridinyl and 1,4-dithianaphthalenyl.

The heterocyclic ring residue having 1–2 hetero atoms selected from the group consisting of nitrogen atom, oxygen atom and sulfur atom, which has 1–3 groups selected from the group consisting of carboxyl group and lower alkoxy groups, include, for example, 4-carboxy-2-furyl, 5-carboxy-2-furyl, 4-carboxy-2-pyridyl, 6-carboxy-2-pyridyl, 4-methoxy-5-carboxy-2-thiophenyl, 4-carboxy-2-thiazolyl, 2-carboxy-4-pyridyl and 4-carboxy-2-pyrimidyl.

Of the thiazole derivatives represented by the general formula (1), those compounds having basic group react easily with pharmacologically acceptable ordinary acids to form respective salts. Such acids can be exemplified by inorganic acids such as sulfuric acid, nitric acid, hydrochloric acid, phosphoric acid, hydrobromic acid and the like; and organic acids such as acetic acid, p-toluenesulfonic acid, ethanesulfonic acid, oxalic acid, maleic acid, fumaric acid, malic acid, tartaric acid, citric acid, succinic acid, benzoic acid and the like.

Of the thiazole derivatives represented by the general formula (1), those compounds having acidic group react easily with pharmacologically acceptable ordinary basic compounds to form respective salts. Such basic compounds include, for example, sodium hydroxide, potassium hydroxide, calcium hydroxide, sodium carbonate and potassium hydrogencarbonate.

Needless to say, the compounds of the present invention include optical isomers.

Each of the compounds of the general formula (1) is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, capsules, suppositories, an injection (e.g. solution or suspension), etc. In preparing tablets, there can be used various carriers known in the art. The carriers can be exemplified by excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers known in the art. The carriers can be exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used various carriers known in the art. The carriers can be exemplified by a polyethylene glycol, cacao butter, a higher alcohol, a higher alcohol ester, gelatin and a semi-synthetic glyceride. Capsules can be prepared ordinarily by mixing the above-mentioned active ingredient with various carriers mentioned above and filling the resulting mixture into hard gelatin capsules, soft capsules or the like, according to an ordinary method. In preparing an injection (solution, emulsion or suspension), it is sterilized and is preferably made isotonic to the blood. In preparing the solution, emulsion or suspension, there can be used all diluents ordinarily used in the art, such as water, ethyl alcohol, macrogol, propylene glycol, ethoxylated isostearyl alcohol, polyoxy-isostearyl alcohol and polyoxyethylene sorbitan-fatty acid esters. In this case, the injection may contain sodium chloride, glucose or glycerine in an amount sufficient to make the injection isotonic, and may further contain a solubilizing adjuvant, a buffer solution, a soothing agent, etc. all ordinarily used. The pharmaceutical preparation may furthermore contain, as necessary, a coloring agent, a preservative, a perfume, a flavoring agent, a sweetening agent and other drugs.

The amount of the active ingredient compound to be contained in the pharmaceutical preparation of the present invention is not particularly restricted and can be appropriately selected from a wide range, but the desirable amount is generally about 1–70% by weight in the pharmaceutical preparation.

The method for administering the pharmaceutical preparation of the present invention is not particularly restricted. The method is decided depending upon the form of preparation, the age, sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation of the present invention is appropriately selected depending upon the administration method, the age, sex and other conditions of patient, the disease condition of patient, etc., but the desirable dose is generally about 0.2–200 mg per kg of body weight per day in terms of the amount of the active ingredient, i.e. the compound of general formula (1) or the salt thereof.

EXAMPLES

The present invention is hereinafter described specifically by way of Reference Examples, Examples, Pharmacological Tests and Preparation Examples.

Reference Example 1

To a solution of 0.88 g of 6-acetyl-3-acetyloxy-2-ethoxycarbonylpyridine in 8.8 ml of acetic acid was added 0.19 ml of bromine dropwise, and the mixture was stirred at 75° C. for 5 minutes. Evaporation of the solvent gave 0.77 g of 6-(2-bromoacetyl)-2-ethoxycarbonyl-3-hydroxypyridine hydrobromide.

Reference Example 2

5-(2-Bromoacetyl)-2-methoxycarbonylfuran was prepared from 5-acetyl-2-methoxycarbonylfuran using the procedure given in Reference Example 1.

Reference Example 3

A solution of 29 g of 3,4-diethoxybenzonitrile and 23 g of thioacetamide in 120 ml of 10% hydrochloric acid-DMF was sirred at 90° C. for 3 hours and then 130° C. for 5 hours. After evaporation of the solvent, the residue was washed with diethyl ether (2×100 ml) and water (2×100 ml). The resulting crystals were collected by filtration and dried to obtain 21.7 g of 3,4-diethoxythiobenzamide.

Reference Example 4

4-Methoxy-3-propoxythiobenzamide was prepared from 4-methoxy-3-propoxybenzonitrile using the procedure given in Reference Example 3.

Reference Example 5

To a solution of 877 mg of 5-(2-bromoacetyl)-2-methoxycarbonylfuran in 40 ml of methanol was added 800 mg of 4-methoxy-3-propoxythiobenzamide, and the mixture was refluxed for 1 hour. The reaction mixture was concentrated approximately ¼, then added diethyl ether. After cooling the solution, a precipitate was collected by filtration and dried to obtain 1.05 g of 2-(4-methoxy-3-propoxyphenyl)- 4-(5-methoxycarbonyl-2-furyl)thiazole as a brown powder. mp. 141.0–142.0° C.

Reference Example 6–36

Using appropriate starting materials and using procedures similar to those used in the above Reference Examples, there were obtained the compounds shown in Table 1 to Table 6.

TABLE 1

| Reference Example | $R^1$ | $R^2$ | Properties |
|---|---|---|---|
| 6 | 4-methyl-2-methoxy-3-propoxyphenyl (OCH$_3$, O(CH$_2$)$_2$CH$_3$) | H$_3$COOC-furan-methyl (5-methoxycarbonyl-2-furyl with methyl) | Melting point: 141.0–142.0° C. Brown powder |
| 7 | 4-methyl-2,3-diethoxyphenyl (OC$_2$H$_5$, OC$_2$H$_5$) | H$_3$COOC-furan-methyl | Melting point: 138.0–139.0° C. Light yellow powder |
| 8 | 4-methyl-2,3-diethoxyphenyl (OC$_2$H$_5$, OC$_2$H$_5$) | 3-methyl-4-methoxy-5-methoxycarbonyl-phenyl (CH$_3$, CH$_3$O, COOCH$_3$) | Melting point: 82.5–85.0° C. Light yellow powder |
| 9 | 4-methyl-2,3-diethoxyphenyl (OC$_2$H$_5$, OC$_2$H$_5$) | 3-ethyl-4-methoxy-5-methoxycarbonyl-phenyl (C$_2$H$_5$, CH$_3$O, COOCH$_3$) | Melting point: 83.5–85.5° C. White powder |
| 10 | 4-methyl-2,3-diethoxyphenyl (OC$_2$H$_5$, OC$_2$H$_5$) | 3-allyl-2-hydroxy-5-methyl-phenyl with COOCH$_3$ (CH$_2$, HO, COOCH$_3$) | Identical with the properties of a compound mentioned in JP-A-5-51318 |
| 11 | 4-methyl-2,3-diethoxyphenyl (OC$_2$H$_5$, OC$_2$H$_5$) | 3-(1,2-dihydroxy-2-methylpropyl)-4-methoxy-5-methoxycarbonyl-phenyl (HO, OH, CH$_3$, CH$_3$, CH$_3$O, COOCH$_3$) | Melting point: 95.0–97.5° C. White powder |

TABLE 2
| Reference Example | R$^1$ | R$^2$ | Properties |
|---|---|---|---|
| 12 | 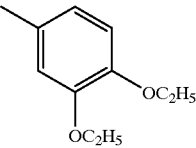 | 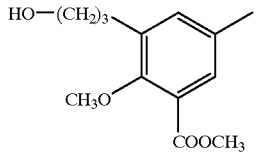 | Light brown oil NMR (1) |
| 13 | 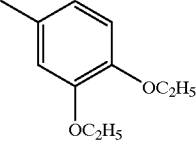 | 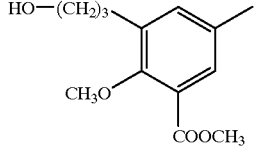 | Light yellow viscous oil NMR (2) |
| 14 | 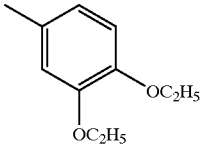 | 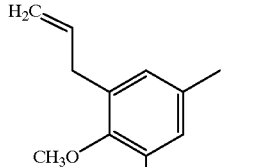 | Colorless viscous oil NMR (3) |
| 15 | 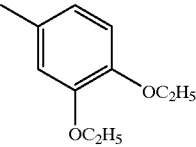 | 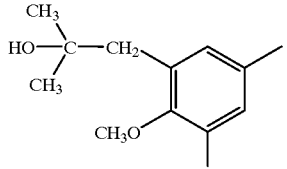 | Colorless viscous oil NMR (4) |
| 16 | 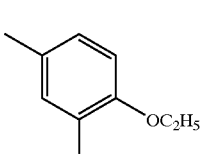 | 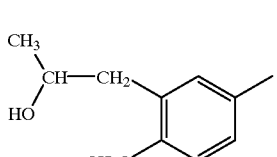 | Colorless viscous oil NMR (5) |
| 17 | 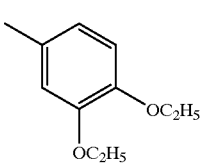 | 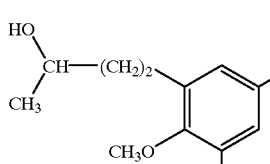 | Colorless viscous oil NMR (6) |

TABLE 3

| Reference Example | R¹ | R² | Properties |
|---|---|---|---|
| 18 | 4-methyl-2,3-bis(OC₂H₅)phenyl | CH(CH₃)₂-CH(OH)- attached to 3-methoxy-4-methyl-6-(COOCH₃)phenyl with methyl | Melting point: 104.0–106.5° C. Light yellow needles |
| 19 | 4-methyl-2-OCH₃-3-OC₂H₅-phenyl | 5-methyl-2-(H₃COOC)furan | Melting point: 158.5–159.5° C. Light yellow powder |
| 20 | 4-methyl-2,3-bis(OC₂H₅)phenyl | (CH₃)₂N-CH₂- attached to 3-methoxy-4-methyl-6-(COOCH₃)phenyl | Light brown solid NMR (7) |
| 21 | 4-methyl-2,3-bis(OC₂H₅)phenyl | H₂N-CH₂- attached to 3-methoxy-4-methyl-6-(COOCH₃)phenyl | Light yellow oil NMR (8) |
| 22 | 4-methyl-2-OCH₃-3-OC₂H₅-phenyl | 3-OCH₃-5-methyl-2-(H₃COOC)thiophene | Melting point: 179.5–180.5° C. Light brown needles |
| 23 | 4-methyl-2-OCH₃-3-OC₂H₅-phenyl | 5-methyl-3-(H₃COOC)furan | Melting point: 165.0–167.0° C. White powder |

TABLE 4

| Reference Example | R¹ | R² | Properties |
|---|---|---|---|
| 24 | 4-methyl-2,3-bis(OC₂H₅)phenyl | HOCH₂-C(CH₃)(OH)-CH₂- attached to 3-methoxy-4-methyl-6-(COOCH₃)phenyl | Colorless amorphous NMR (9) |

TABLE 4-continued
| Reference Example | R¹ | R² | Properties |
|---|---|---|---|
| 25 | 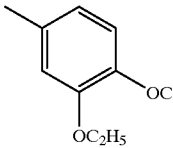 | 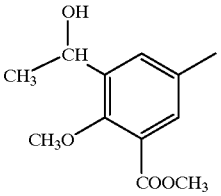 | Yellow amorphous NMR (10) |
| 26 | 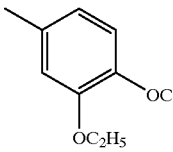 | 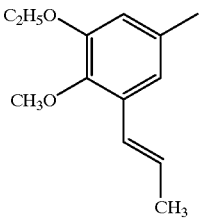 | Light yellow viscous oil NMR (11) |
| 27 | 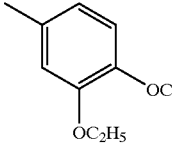 | 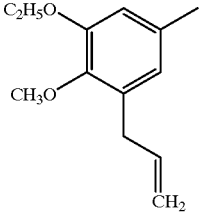 | Light yellow powder NMR (12) |
| 28 | 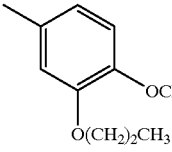 | 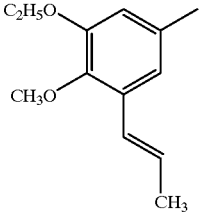 | Light yellow viscous oil NMR (13) |
TABLE 5
| Reference Example | R¹ | R² | Properties |
|---|---|---|---|
| 29 | 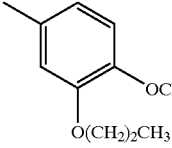 | 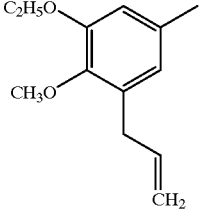 | Melting point: 106.0–107.0° C. Light yellow powder |
| 30 | 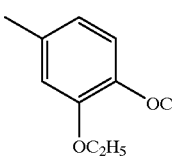 | 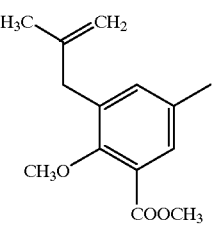 | Yellow oil NMR (14) |

TABLE 5-continued

| Reference Example | R¹ | R² | Properties |
|---|---|---|---|
| 31 | 4-methyl-2,3-bis(OC₂H₅)phenyl | (CH₃)₂CHCH₂-, CH₃O-, COOCH₃ substituted methylphenyl | Colorless viscous oil NMR (15) |
| 32 | 4-methyl-2,3-bis(OC₂H₅)phenyl | CH₃(CH₂)₂-, CH₃O-, COOC₂H₅ substituted methylphenyl | Colorless viscous oil NMR (16) |

TABLE 6

| Reference Example | R¹ | R² | Properties |
|---|---|---|---|
| 33 | 4-methyl-2,3-bis(OC₂H₅)phenyl | CH₃—CH=CH-, CH₃O-, COOCH₃ substituted methylphenyl | Brown oil NMR (17) |
| 34 | 4-methyl-2,3-bis(OC₂H₅)phenyl | CH₂=CH-, CH₃O-, COOCH₃ substituted methylphenyl | Light yellow oil NMR (18) |
| 35 | 4-methyl-2,3-bis(OC₂H₅)phenyl | CH₃O-, CH₃O-, CH=CH-CH₃ substituted methylphenyl | Melting point: 101.5–105.5° C. Light yellow powder |

The above-obtained compounds had the following NMR spectra.

NMR(1): $^1$H-NMR (CDCl$_3$) δ ppm;

1.49 (3H, t, J=7.0 Hz), 1.51 (3H, t, J=7.0 Hz), 1.86 (3H, d, J=1.2 Hz), 1.98 (3H, d, J=1.2 Hz), 3.81 (3H, s), 3.95 (3H, s), 4.12 (2H, q, J=7.0 Hz), 4.22 (2H, q, J=7.0 Hz), 6.36 (1H, br-s), 6.92 (1H, d, J=8.3 Hz), 7.37 (1H, s), 7.53 (1H, dd, J=2.0 Hz, J=8.3 Hz), 7.61 (1H, d, J=2.0 Hz), 7.97 (1H, d, J=2.3 Hz), 8.22 (1H, d, J=2.3 Hz).

NMR(2): $^1$H-NMR (CDCl$_3$) δ ppm;

1.50 (3H, t, J=7.0 Hz), 1.52 (3H, t, J=7.0 Hz), 1.74–2.04 (3H, m), 2.86 (2H, t, J=7.7 Hz), 3.58–3.72 (2H, m), 3.89 (3H, s), 3.96 (3H, s), 4.16 (2H, q, J=7.0 Hz), 4.23 (2H, q, J=7.0 Hz), 6.93 (1H, d, J=8.4 Hz), 7.40 (1H, s), 7.54 (1H, dd, J=2.1 Hz, J=8.4 Hz), 7.60 (1H, d, J=2.1 Hz), 8.02 (1H, d, J=2.3 Hz), 8.23 (1H, d, J=2.4 Hz).

NMR(3): $^1$H-NMR (CDCl$_3$) δ ppm;

1.49 (3H, t, J=7.0 Hz), 1.52 (3H, t, J=7.0 Hz), 3.53 (2H, d, J=6.4 Hz), 3.86 (3H, s), 3.96 (3H, s), 4.16 (2H, q, J=7.0 Hz), 4.23 (2H, q, J=7.0 Hz), 5.02–5.21 (2H, m), 5.91–6.19 (1H, m), 6.93 (1H, d, J=8.4 Hz), 7.39 (1H, s), 7.53 (1H, dd, J=2.1 Hz, J=8.4 Hz), 7.61 (1H, d, J=2.1 Hz), 7.98 (1H, d, J=2.4 Hz), 8.26 (1H, d, J=2.4 Hz).

NMR(4): $^1$H-NMR (CDCl$_3$) δ ppm;

1.27 (6H, s), 1.50 (3H, t, J=7.0 Hz), 1.51 (3H, t, J=7.0 Hz), 2.61 (1H, br-s), 2.95 (2H, s), 3.89 (3H, s), 3.96 (3H, s), 4.16 (2H, q, J=7.0 Hz), 4.22 (2H, q, J=7.0 Hz), 6.93 (1H, d, J=8.3

Hz), 7.40 (1H, s), 7.54 (1H, dd, J=2.1 Hz), J=8.3 Hz), 7.59 (1H, d, J=2.1 Hz), 8.00 (1H, d, J=2.4 Hz), 8.31 (1H, d, J=2.4 Hz).

NMR(5): $^1$H-NMR (CDCl$_3$) δ ppm;

1.29 (3H, d, J=6.2 Hz), 1.49 (3H, t, J=7.0 Hz), 1.52 (3H, t, J=7.0 Hz), 2.08 (1H, br-s), 2.75–3.05 (2H, m), 3.89 (3H, s), 3.97 (3H, s), 4.08–4.29 (1H, m), 4.16 (2H, q, J=7.0 Hz), 4.23 (2H, q, J=7.0 Hz), 6.93 (1H, d, J=8.4 Hz), 7.40 (1H, s), 7.54 (1H, dd, J=2.1 Hz, J=8.4 Hz), 7.61 (1H, d, J=2.1 Hz), 8.02 (1H, d, J=2.3 Hz), 8.28 (1H, d, J=2.3 Hz).

NMR(6): $^1$H-NMR (CDCl$_3$) δ ppm;

1.23 (3H, d, J=6.2 Hz), 1.49 (3H, t, J=7.0 Hz), 1.51 (3H, t, J=7.0 Hz), 1.71–1.98 (3H, m), 2.86 (2H, t, J=8.0 Hz), 3.69–3.86 (1H, m), 3.89 (3H, s), 3.96 (3H, s), 4.16 (2H, q, J=7.0 Hz), 4.23 (2H, q, J=7.0 Hz), 6.93 (1H, d, J=8.4 Hz), 7.40 (1H, s), 7.54 (1H, dd, J=2.1 Hz, J=8.4 Hz), 7.60 (1H, d, J=2.1 Hz), 8.01 (1H, d, J=2.3 Hz), 8.23 (1H, d, J=2.3 Hz).

NMR(7): $^1$H-NMR (CDCl$_3$) δ ppm;

1.49 (3H, t, J=7.0 Hz), 1.51 (3H, t, J=7.0 Hz), 2.30 (6H, s), 3.56 (2H, s), 3.88 (3H, s), 3.96 (3H, s), 4.16 (2H, q, J=7.0 Hz), 4.23 (2H, q, J=7.0 Hz), 6.92 (1H, d, J=8.4 Hz), 7.43 (1H, s), 7.54 (1H, dd, J=2.1 Hz, J=8.4 Hz), 7.61 (1H, d, J=2.1 Hz), 8.15 (1H, d, J=2.4 Hz), 8.35 (1H, d, J=2.4 Hz).

NMR(8): $^1$H-NMR (CDCl$_3$) δ ppm;

1.49 (3H, t, J=7.0 Hz) 1.51 (3H, t, J=7.0 Hz), 3.90 (3H, s), 3.96 (3H, s), 3.99 (2H, s), 4.15 (2H, q, J=7.0 Hz), 4.22 (2H, q, J=7.0 Hz) 6.92 (1H, d, J=8.3 Hz), 7.43 (1H, s), 7.53 (1H, dd, J=2.1 Hz, J=8.3 Hz), 7.59 (1H, d, J=2.1 Hz), 8.14 (1H, d, J=2.3 Hz), 8.29 (1H, d, J=2.3 Hz).

NMR(9): $^1$H-NMR (CDCl$_3$) δ ppm;

1.19 (3H, s), 1.50 (3H, t, J=7.0 Hz), 1.52 (3H, t, J=7.0 Hz), 2.72 (1H, t, J=6.8 Hz), 2.91 (1H, d, J=13.5 Hz), 3.01 (1H, s), 3.07 (1H, d, J=13.5 Hz), 3.37 (2H, dd, J=2.1 Hz, J=6.8 Hz), 3.92 (1H, s), 3.97 (1H, s), 4.16 (2H, q, J=7.0 Hz), 4.22 (2H, q, J=7.0 Hz), 6.93 (1H, d, J=8.3 Hz), 7.42 (1H, s), 7.54 (1H, dd, J=2.1 Hz, J=8.3 Hz), 7.59 (1H, d, J=2.1 Hz), 8.02 (1H, d, J=2.3 Hz), 8.32 (1H, d, J=2.3 Hz).

NMR(10): $^1$H-NMR (CDCl$_3$) δ ppm;

1.50 (3H, t, J=7.0 Hz) 1.52 (3H, t, J=7.0 Hz), 1.58 (3H, d, J=6.5 Hz), 2.32 (1H, d, J=4.2 Hz), 3.91 (3H, s), 3.97 (3H, s), 4.16 (2H, q, J=7.0 Hz), 4.22 (2H, q, J=7.0 Hz), 5.21–5.38 (1H, m), 6.92 (1H, d, J=8.4 Hz), 7.43 (1H, s), 7.54 (1H, dd, J=2.1 Hz, J=8.4 Hz), 7.61 (1H, d, J=2.1 Hz), 8.25 (1H, d, J=2.2 Hz), 8.33 (1H, d, J=2.2 Hz).

NMR(11): $^1$H-NMR (CDCl$_3$) δ ppm;

1.41–1.59 (9H, m), 1.94 (3H, dd, J=1.6 Hz, J=6.6 Hz), 6.22–6.51 (1H, m), 6.68–6.85 (1H, m), 6.92 (1H, d, J=8.4 Hz), 7.32 (1H, s), 7.41 (1H, d, J=2.0 Hz), 7.54 (1H, dd, J=2.0 Hz, J=8.4 Hz), 7.60 (2H, d, J=2.0 Hz).

NMR(12): $^1$H-NMR (CDCl$_3$) δ ppm;

1.49 (3H, t, J=7.0 Hz), 1.50 (3H, t, J=7.0 Hz), 1.51 (3H, t, J=7.0 Hz), 3.47 (2H, d, J=6.4 Hz), 3.87 (1H, s), 4.16 (2H, q, J=7.0 Hz), 4.19 (2H, q, J=7.0 Hz), 4.22 (2H, q, J=7.0 Hz), 5.00–5.19 (2H, m), 5.91–6.15 (1H, m), 6.92 (1H, d, J=8.4 Hz), 7.30 (1H, s), 7.33 (1H, d, J=2.0 Hz), 7.44 (1H, d, J=2.0 Hz), 7.53 (1H, dd, J=2.1 Hz, J=8.4 Hz), 7.60 (1H, d, J=2.1 Hz).

NMR(13): $^1$H-NMR (CDCl$_3$) δ ppm;

1.08 (3H, t, J=7.5 Hz), 1.50 (3H, t, J=7.0 Hz), 1.82–2.05 (5H, m), 3.85 (3H, s), 3.93 (3H, s), 4.11 (2H, t, J=6.9 Hz), 4.19 (2H, q, J=7.0 Hz), 6.22–6.51 (1H, m), 6.65–6.83 (1H, m), 6.93 (1H, d, J=8.3 Hz), 7.33 (1H, s), 7.41 (1H, d, J=2.0 Hz), 7.55 (1H, dd, J=2.0 Hz, J=8.3 Hz), 7.60 (2H, d, J=2.0 Hz).

NMR(14): $^1$H-NMR (CDCl$_3$) δ ppm;

1.49 (3H, t, J=7.0 Hz), 1.51 (3H, t, J=7.0 Hz), 1.78 (3H, s), 3.47 (2H, s), 3.85 (3H, s), 3.96 (3H, s), 4.16 (2H, q, J=7.0 Hz), 4.23 (2H, q, J=7.0 Hz), 4.69 (1H, s), 4.88 (1H, s), 6.92 (1H, d, J=8.4 Hz), 7.39 (1H, s), 7.53 (1H, dd, J=2.1 Hz, J=8.4 Hz), 7.61 (1H, d, J=2.1 Hz), 7.96 (1H, d, J=2.3 Hz), 8.28 (1H, d, J=2.3 Hz).

NMR(15): $^1$H-NMR (CDCl$_3$) δ ppm;

0.95 (6H, d, J=6.6 Hz), 1.49 (3H, t, J=7.0 Hz), 1.51 (3H, t, J=7.0 Hz), 1.90–2.14 (1H, m), 2.61 (2H, d, J=7.3 Hz), 3.85 (3H, s), 3.96 (3H, s), 4.15 (2H, q, J=7.0 Hz), 4.22 (2H, q, J=7.0 Hz), 6.92 (1H, d, J=8.3 Hz), 7.38 (1H, s), 7.55 (1H, dd, J=2.1 Hz, J=8.3 Hz), 7.60 (1H, d, J=2.1 Hz), 7.93 (1H, d, J=2.4 Hz), 8.23 (1H, d, J=2.4 Hz).

NMR(16): $^1$H-NMR (CDCl$_3$) δ ppm;

1.01 (3H, t, J=7.4 Hz), 1.44 (3H, t, J=7.1 Hz), 1.49 (3H, t, J=7.0 Hz), 1.51 (3H, t, J=7.0 Hz), 1.71 (2H, sextet, J=7.4 Hz), 2.72 (2H, t, J=7.4 Hz), 3.87 (3H, s), 4.16 (2H, q, J=7.0 Hz), 4.22 (2H, q, J=7.0 Hz), 4.43 (2H, q, J=7.1 Hz), 6.92 (1H, d, J=8.4 Hz), 7.39 (1H, s), 7.53 (1H, dd, J=2.1 Hz, J=8.4 Hz), 7.62 (1H, d, J=2.1 Hz), 7.97 (1H, d, J=2.3 Hz), 8.21 (1H, d, J=2.3 Hz).

NMR(17): $^1$H-NMR (CDCl$_3$) δ ppm;

1.49 (3H, t, J=7.0 Hz), 1.51 (3H, t, J=7.0 Hz), 1.97 (3H, dd, J=1.6 Hz, J=6.5 Hz), 3.85 (3H, s), 3.96 (3H, s), 4.16 (2H, q, J=7.0 Hz), 4.23 (2H, q, J=7.0 Hz), 6.41 (1H, dq, J=6.5 Hz, J=15.9 Hz), 6.75 (1H, dd, J=1.6 Hz, J=15.9 Hz), 6.93 (1H, d, J=8.3 Hz), 7.40 (1H, s), 7.55 (1H, dd, J=2.1 Hz, J=8.3 Hz), 7.60 (1H, d, J=2.1 Hz), 8.21 (2H, s).

NMR(18): $^1$H-NMR (CDCl$_3$) δ ppm;

1.49 (3H, t, J=7.0 Hz), 1.51 (3H, t, J=7.0 Hz), 3.87 (3H, s), 3.96 (3H, s), 4.16 (2H, q, J=7.0 Hz), 4.23 (2H, q, J=7.0 Hz), 5.44 (1H, dd, J=1.1 Hz, J=11.1 Hz), 5.92 (1H, dd, J=1.1 Hz, J=17.7 Hz), 6.93 (1H, d, J=8.3 Hz), 7.09 (1H, dd, J=11.1 Hz, J=17.7 Hz), 7.42 (1H, s), 7.54 (1H, dd, J=2.1 Hz, J=8.3 Hz), 7.61 (1H, d, J=2.1 Hz), 8.28 (2H, br-s).

Example 1

To a suspension of 970 mg of 2-(4-methoxy-3-propoxyphenyl)-4-(5-methoxycarbonyl-2-furyl)thiazole in 30 ml of methanol was added 20 ml of 1,4-dioxane and 5 ml of a 5 N aqueous sodium hydroxide solution. The reaction mixture was refluxed for 3 hours, then concentrated approximately 1/10. Water was added to the residue, and washed with ethyl acetate. To the aqueous layer was acidified with 5 N hydrochloric acid, and extracted with ethyl acetate. The combined organic layer was washed with water and a saturated aqueous sodium chloride solution, and dried with magnesium sulfate. Evaporation the solution, the residue was recrystallized from ethyl acetate to obtain 420 mg of 2-(4-methoxy-3-propoxyphenyl)-4-(5-carbonyl-2-furyl)thiazole as a white powder. mp. 191.0–192.0° C.

Examples 2–35

Using appropriate starting materials and using procedures similar to that used in Example 1, there were obtained the compounds shown in Table 7 to Table 12.

TABLE 7

| Example | R¹ | R² | Properties |
|---|---|---|---|
| 1 | 4-methyl-2-methoxy-3-propoxyphenyl (OCH₃, O(CH₂)₂CH₃) | 5-methyl-2-carboxyfuran (HOOC-furan-CH₃) | Melting point: 191.0–192.0° C. White powder |
| 2 | 4-methyl-2,3-diethoxyphenyl (OC₂H₅, OC₂H₅) | 6-methyl-2-carboxypyridine (COOH, N) | Melting point: 182.0–184.0° C. White powder |
| 3 | 4-methyl-2,3-diethoxyphenyl (OC₂H₅, OC₂H₅) | 4-methyl-2-carboxyfuran (HOOC-furan-CH₃) | Melting point: 163.0–167.0° C. Light yellow powder |
| 4 | 4-methyl-2,3-diethoxyphenyl (OC₂H₅, OC₂H₅) | 3,5-dimethyl-2-methoxy-6-carboxyphenyl (CH₃, CH₃O, COOH) | Melting point: 202.0–203.0° C. White powder |
| 5 | 4-methyl-2,3-diethoxyphenyl (OC₂H₅, OC₂H₅) | 3-ethyl-5-methyl-2-methoxy-6-carboxyphenyl (C₂H₅, CH₃O, COOH) | Melting point: 201.0–202.0° C. White powder |
| 6 | 4-methyl-2,3-diethoxyphenyl (OC₂H₅, OC₂H₅) | 3-allyl-5-methyl-2-methoxy-6-carboxyphenyl (CH₂=CH-CH₂, CH₃O, COOH) | Melting point: 153.0–154.0° C. Light yellow granules |

TABLE 8

| Example | R¹ | R² | Properties |
|---|---|---|---|
| 7 | 4-methyl-2,3-diethoxyphenyl (OC₂H₅, OC₂H₅) | 3-(1,2-dihydroxy-2-methylpropyl)-5-methyl-2-methoxy-6-carboxyphenyl (HO, OH, CH₃-C(CH₃)-CH, CH₃O, COOH) | Light yellow amorphous NMR (1) |

TABLE 8-continued
| Example | R¹ | R² | Properties |
|---|---|---|---|
| 8 | 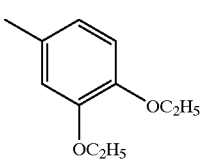 | 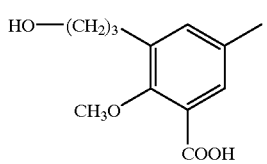 | Melting point: 109.5–111.5° C. White powder |
| 9 | 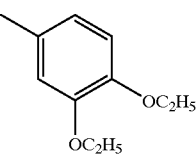 | 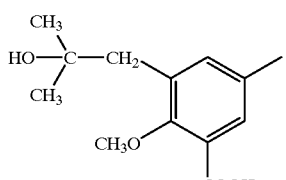 | Melting point: 137.0–139.0° C. White powder |
| 10 | 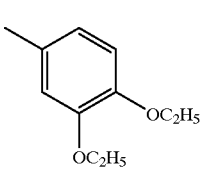 | 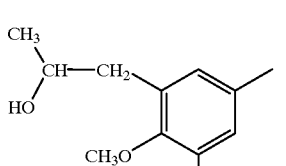 | Melting point: 135.0–138.0° C. White powder |
| 11 | 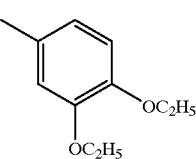 | 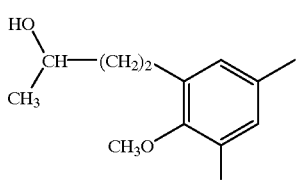 | Melting point: 110.0–112.5° C. White powder |
| 12 | 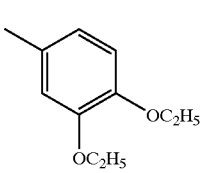 | 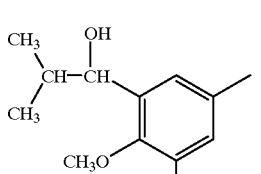 | Melting point: 165.0–167.0° C. Colorless needles |
TABLE 9
| Example | R¹ | R² | Properties |
|---|---|---|---|
| 13 | 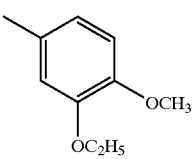 | 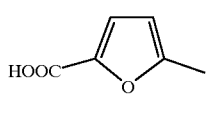 | Melting point: 204.5–206.5° C. Colorless needles |
| 14 | 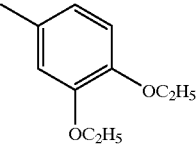 | 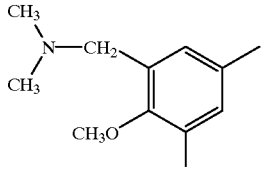 | Form: monohydrochloride Yellow amorphous NMR (2) |

TABLE 9-continued
| Example | R¹ | R² | Properties |
|---|---|---|---|
| 15 | 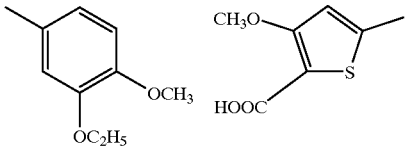 | 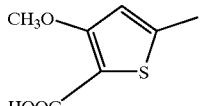 | Melting point: 201.0–202.0° C. Light yellow needles |
| 16 | 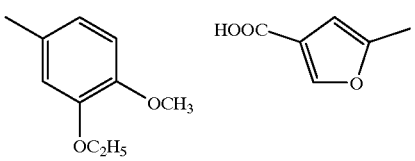 | 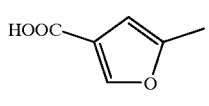 | Melting point: 206.0–207.0° C. White powder |
| 17 | 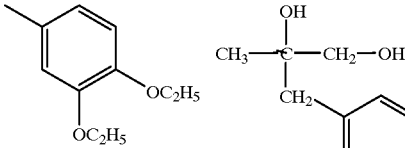 | 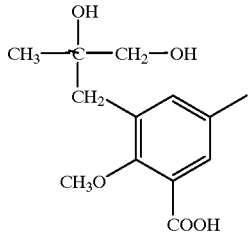 | Melting point: 134.0–136.0° C. White powder |
| 18 | 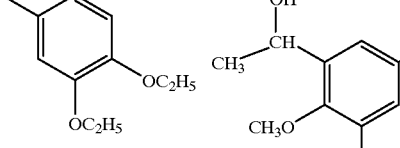 | 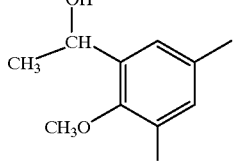 | Melting point: 189.0–190.0° C. Light yellow plates |
TABLE 10
| Example | R¹ | R² | Properties |
|---|---|---|---|
| 19 | 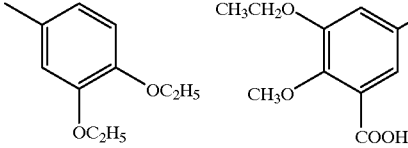 | 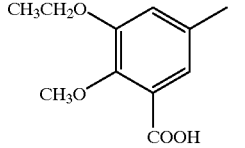 | Melting point: 147.5–149.0° C. Light yellow prisms |
| 20 | 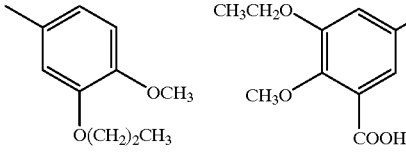 | 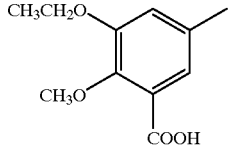 | Melting point: 139.0–141.0° C. Light yellow prisms |
| 21 | 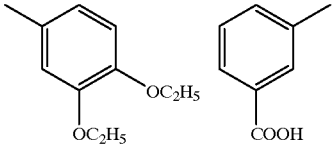 | 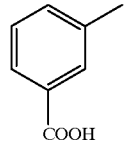 | Identical with the properties of a compound mentioned in JP-A-5-51318 |

TABLE 10-continued

| Example | R¹ | R² | Properties |
|---|---|---|---|
| 22 | 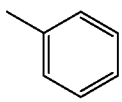 | 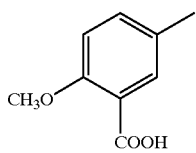 | Identical with the properties of a compound mentioned in JP-A-5-51318 |
| 23 | 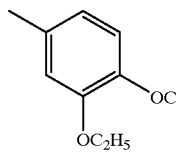 | 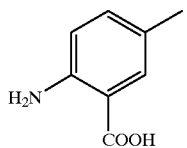 | Identical with the properties of a compound mentioned in JP-A-5-51318 |
| 24 | 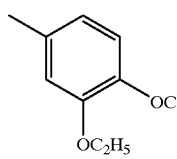 | 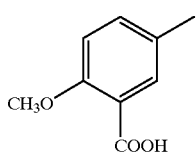 | Identical with the properties of a compound mentioned in JP-A-5-51318 |
| 25 | 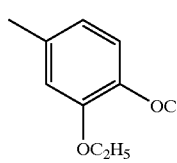 | 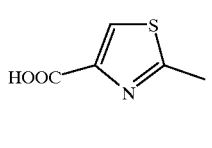 | Identical with the properties of a compound mentioned in JP-A-6-65222 |

TABLE 11

| Example | R¹ | R² | Properties |
|---|---|---|---|
| 26 | 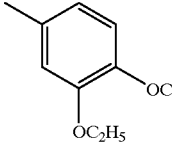 | 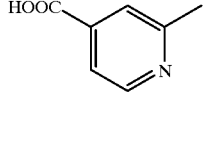 | Identical with the properties of a compound mentioned in JP-A-6-65222 |
| 27 | 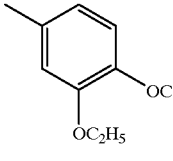 | 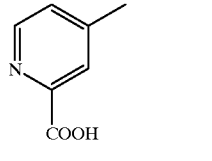 | Identical with the properties of a compound mentioned in JP-A-6-65222 |
| 28 | 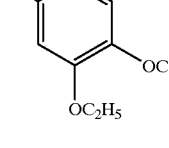 | 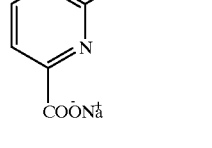 | Identical with the properties of a compound mentioned in JP-A-6-65222 |
| 29 | 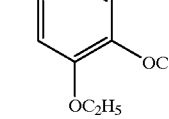 | 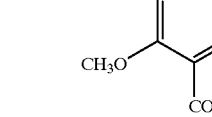 | Melting point: 65.0–68.0° C. Light yellow powder |

TABLE 11-continued

| Example | R¹ | R² | Properties |
|---|---|---|---|
| 30 | 4-methyl-2,3-bis(OC₂H₅) phenyl | 3-methyl-4-isobutyl-6-methoxy-2-carboxyphenyl (with (CH₃)₂CHCH₂ and CH₃O, COOH) | Melting point: 163.0–165.0° C. White powder |
| 31 | 4-methyl-2,3-bis(OC₂H₅) phenyl | 3-methyl-4-propyl-6-methoxy-2-carboxyphenyl (with CH₃(CH₂)₂ and CH₃O, COOH) | Melting point: 145.0–147.0° C. White powder |

TABLE 12

| Example | R¹ | R² | Properties |
|---|---|---|---|
| 32 | 4-methyl-2,3-bis(OC₂H₅) phenyl | 3-methyl-4-(CH₃—CH=CH)-6-methoxy-2-carboxyphenyl | Melting point: 176.0–179.0° C. Colorless needles |
| 33 | 4-methyl-2,3-bis(OC₂H₅) phenyl | 3-methyl-4-(CH₂=CH)-6-methoxy-2-carboxyphenyl | Melting point: 208.0–210.0° C. White powder |
| 34 | 4-methyl-2,3-bis(OC₂H₅) phenyl | substituted phenyl with CH₂O, COOH, OCH₃ | Melting point: 175.5–177.5° C. Colorless prisms |
| 35 | 4-methyl-2,3-bis(OC₂H₅) phenyl | 3-methyl-4,5-bis(CH₃O)-2-carboxyphenyl | Melting point: 188.5–190.0° C. White powder |

The above-obtained compounds had the following NMR spectra.

NMR(1): ¹H-NMR (CDCl₃) δ ppm;
1.14 (3H, s), 1.35 (3H, s), 1.49 (3H, t, J=7.0 Hz), 1.50 (3H, t, J=7.0 Hz), 3.84 (3H, s), 4.15 (2H, q, J=7.0 Hz), 4.21 (2H, q, J=7.0 Hz), 4.96 (1H, s), 6.91 (1H, d, J=8.3 Hz), 7.44 (1H, s), 7.52 (1H, dd, J=2.1 Hz, J=8.3 Hz), 7.58 (1H, d, J=2.1 Hz), 8.37 (1H, d, J=2.4 Hz), 8.55 (1H, d, J=2.4 Hz).

NMR(2): ¹H-NMR (DMSO-D₆) δ ppm;
1.34 (3H, t, J=6.8 Hz), 1.36 (3H, t, J=6.8 Hz), 2.74 (3H, s), 2.76 (3H, s), 3.86 (3H, s), 4.08 (2H, q, J=6.8 Hz), 4.14 (2H, q, J=6.8 Hz), 4.29–4.56 (2H, m), 7.06 (1H, d, J=8.9 Hz), 7.35–7.72 (2H, m), 8.16 (1H, s), 8.39 (1H, d, J=1.9 Hz), 8.67 (1H, d, J=1.9 Hz), 10.95 (1H, br-s).

Pharmacological Test 1 (Adhesion-inhibiting action 1)

A test compound was dissolved in 0.1 M sodium hydroxide. To the resulting solution was added a 9-fold volume of PBS (phosphate buffered saline) of Dulbecco formula (a product of Takara Co.) to prepare a 1 mM test compound solution. This solution was diluted with 0.1 M sodium hydroxide/PBS (1:9) to prepare a 0.1 mM test compound solution and a 0.01 mM test compound solution. The two test compound solutions were each diluted 40-fold with a RPMI-1640 medium [containing 10% FCS (fetal calf serum)]. Separately, N-formylmethionylleucylphenylalanine (fMLP) (2 mM dissolved in dimethylformamide) was diluted with the RPMI- 1640 medium (containiing 10% FCS) to prepare a 0.25 mM fMLP solution.

Purified neutrophils were obtained from the whole blood of healthy person by dextran sedimentation, Ficoll-Paque-density density gradient centrifugation and erythrocyte hemolysis; then, were suspended in PBS (3 ml); and labelled with 50 µl of a fluorescence-labelling agent (BCECF-AM, a product of Dojindo Lab.) at room temperature for 1 hour. Human umbilical vein endothelial cells (HUVEC) (a product of Clonetics Co.) were cultivated on a 24-well culture plate, and a test was started when the cells became confluent.

The medium in each well of the culture plate was removed. To the wells were added 0.2 ml of RPMI-1640 (containing 10% FCS) or 0.2 ml of the diluted test compound solution, and 0.2 ml of the fMLP solution. Lastly, $10^6$ fluorescence-labelled neutrophils were added to each well, and each resulting mixture was incubated at 37° C. for 30 minutes. Adherent neutrophils and non-adherent neutrophils cells were collected separately and measured for fluorescent intensity. Using a separately prepared standard line between number of neutrophils and fluorescent intensity, the number of cells was determined and a test compound concentration of 50% adhesion inhibition, i.e. $IC_{50}$ was determined.

The results are shown in Table 13.

TABLE 13

| Test compound | $IC_{50}$ (µM) |
| --- | --- |
| Compound of Example 1 | >10 |
| Compound of Example 2 | 0.6 |
| Compound of Example 3 | >10 |
| Compound of Example 4 | 8.5 |
| Compound of Example 5 | <0.1 |
| Compound of Example 6 | <0.1 |
| Compound of Example 7 | >10 |
| Compound of Example 8 | >10 |
| Compound of Example 9 | >10 |
| Compound of Example 10 | >10 |
| Compound of Example 11 | >10 |
| Compound of Example 12 | 2.5 |
| Compound of Example 13 | 3.0 |
| Compound of Example 21 | >10 |
| Compound of Example 22 | >10 |
| Compound of Example 23 | 5.6 |
| Compound of Example 24 | <0.1 |
| Compound of Example 25 | 5.0 |
| Compound of Example 27 | 2.9 |
| Compound of Example 29 | <0.1 |
| Compound of Example 30 | 4.4 |
| Compound of Example 31 | 0.5 |
| Compound of Example 32 | 0.1 |
| Compound of Example 33 | 0.95 |
| Compound of Example 34 | 5.9 |
| Compound of Example 35 | 0.8 |

Pharmacological Test 2
[Adhesion-inhibiting action 2 (action on appearance of ICAM-1 or VCAM-1 to endothelial cells]

A test compound was dissolved in 0.1 M sodium hydroxide. To the resulting solution was added a 9-fold volume of PBS of Dulbecco formula (a product of Takara Co.) to prepare a 1 mM test compound solution. This solution was diluted with 0.1 M sodium hydroxide/PBS (1:9) to prepare solutions containing 300 µM, 100 µM, 30 µM, 10 µM and 3 µM of the test compound, respectively. The solutions were each diluted 10-fold with RPMI-1640 (containing 10% FCS) to prepare 100 µM, 30 µM, 10 µM, 3 µM, 1 µM and 0.3 µM of test compound solutions.

TNF-α (a product of R & D Systems, 10 µg/ml solution) was diluted with RPMI-1640 (containing 10% FCS) to prepare a 6 ng/ml TNF-α solution. Human aorta endothelial cells (HAEC) and human umbilical vein endothelial cells (HUVEC) were separately cultivated in a 96-well culture plate, and when the cells became confluent, the medium in each well was removed. Then, 50 µl of each of the above-prepared test compound solutions was added to the wells. To positive control wells and negative control wells were added 50 µl of the medium and 100 µl of the medium, respectively. The plate was incubated at 37° C. for 30 minutes. 50 µl of the TNF-α solution prepared above was added to all the wells other than the negative control wells, and the plate was incubated at 37° C. for 24 hours. The medium in each well was removed, and 100 µl of paraformaldehyde (2% in PBS) was added to each well. Fixation was conducted at room temperature for 10 minutes. After washing with a physiological saline solution 6 times, a blocking solution (0.1% BSA (bovine serum albumin)/PBS) was added to each well. The plate was incubated at room temperature for 1 hour. The blocking solution was removed. 100 µl of a primary antibody solution (the antibody diluted 1,000-fold with 0.1% BSA/PBS) was added, and a reaction mixture was incubated at 4° C. for 18 hours. After washing with a physiological saline solution 5 times. 100 µl of a secondary antibody solution (the antibody diluted 1,000-fold with 0.1% BSA/PBS) was added, and a reaction mixture was incubated at room temperature for 2 hours. After washing with a physiological saline solution 5 times, 100 µl of a peroxidase-labelled avidin solution (a product of DAKO Co., diluted 1,000-fold with 0.1% BSA/PBS) was added. The reaction mixture was incubated at room temperature for 1 hour. After washing with a physiological saline solution 5 times, 100 µl of an OPD (o-phenylenediamine dihydrochloride) substrate solution was added and color development was allowed to take place at 37° C. Absorbancy measurement at 492/692 nm was conducted, and a test compound concentration of 50% appearance inhibition of ICAM-1 or VCAM-1, i.e. $IC_{50}$ was determined.

As the test compound, the compound of Example 2 was used. The primary antibody and the secondary antibody were as follows.

Primary antibody:
  Mouse anti-human ICAM-1 (a product of Becton, Dickinson & Co.)
  Mouse anti-human VCAM-1 (a product of Becton, Dickinson & Co.)
Secondary antibody:
  Rabbit anti-human immunoglobulin (a product of DAKO Co.)

The results are shown in Table 14.

TABLE 14

|  | Human aorta endothelial cells (µM) | Human umbilical vein endothelial cells (µM) |
| --- | --- | --- |
| ICAM-1 | 40% inhibition at 100 µM | 25 |
| VCAM-1 | 15 | 30% inhibition at 100 µM |

Pharmacological Test 3 (TNF-α production-inhibiting action)

A test compound was dissolved in 0.1 M sodium hydroxide. Thereto was added a 9-fold volume of PBS (a Dulbecco formula, a product of Takara Co.) to prepare a 1 mM test compound solution. The solution was diluted with 0.1 M sodium hydroxide/PBS (1:9) to prepare 0.1 mM, 0.01 mM, 1 μM, 0.1 μM and 0.01 μM test compound solutions.

A 50 μg/ml lipopolysaccharide (LPS) solution was prepared using RPMI-1640 (containing 10% FCS). A 24-well culture plate was used. 1.35 ml of RPMI-1640 (containing 10% FCS) was added to LPS-unstimulated control wells, and 1.32 ml of RPMI-1640 (containing 10% FCS) was added to LPS-stimulated control wells. To the other wells were added 1.17 ml of RPMI-1640 (containing 10% FCS) and 0.15 ml of each diluted test compound solution prepared above. To all the wells was added 0.15 ml of whole human blood, and the wells were incubated at 37° C. for 30 minutes. Lastly, to all the wells other than the LPS-unstimulated control wells, was added 0.03 ml of the above-prepared LPS solution, and all the wells were incubated at 37° C. for 24 hours. Low-speed centrifugation was conducted, and the supernatant in each well was collected and measured for TNF-α concentration, by the use of a commercial ELISA kit. A test compound concentration of 50% TNF-α production inhibition, i.e. $IC_{50}$ was determined. The results are shown in Table 15.

TABLE 15

| Test compound | $IC_{50}$ (μM) |
| --- | --- |
| Compound of Example 2 | 10 |
| Compound of Example 3 | 6.4 |
| Compound of Example 4 | 36.0 |
| Compound of Example 5 | 40.0 |
| Compound of Example 6 | 33.5 |
| Compound of Example 7 | 7.4 |
| Compound of Example 8 | 3.4 |
| Compound of Example 9 | 0.7 |
| Compound of Example 10 | 4.0 |
| Compound of Example 11 | 19 |
| Compound of Example 12 | 5.7 |
| Compound of Example 13 | 7.5 |
| Compound of Example 14 | 0.47 |
| Compound of Example 15 | 2.3 |
| Compound of Example 16 | 2.7 |
| Compound of Example 17 | 2.0 |
| Compound of Example 18 | 2.3 |
| Compound of Example 19 | 0.88 |
| Compound of Example 20 | 4.7 |

Pharmacological Test 4 (IL-1 production-inhibiting action)

An IL-1 production was measured in the same manner as in Pharmacological Test 3, and a test compound concentration of 50% production inhibition, i.e. $IC_{50}$ was determined. When the test compound was the compound of Example 2, the $IC_{50}$ was 80 μM.

Pharmacological Test 5 (IL-6 production-inhibiting action)

An IL-6 amount produced was measured in the same manner as in Pharmacological Test 3, and a test compound concentration of 50% production inhibition, i.e. $IC_{50}$ was determined. When the test compound was the compound of Example 2, the $IC_{50}$ was 100 μM or higher.

Pharmacological Test 6 (IFN-γ production-inhibiting action)

A test compound was dissolved in 0.1 M sodium hydroxide. Thereto was added a 9-fold volume of PBS (a Dulbecco formula, a product of Takara Co.) to prepare a 1 mM test compound solution. The solution was diluted with 0.1 M sodium hydroxide/PBS (1:9) to prepare 0.1 mM, 0.01 mM, 1 μM, 0.1 μM and 0.01 μM test compound solutions.

A 50 mg/ml concanavalin A (Con A, a product of Seikagaku Co.) solution was prepared using RPMI-1640 (containing 10% FCS). A 24-well culture plate was used. 1.35 ml of RPMI-1640 (containing 10% FCS) was added to Con A-unstimulated control wells, and 1.32 ml of RPMI-1640 (containing 10% FCS) was added to Con A-stimulated control wells. To the other wells were added 1.17 ml of RPMI-1640 (containing 10% FCS) and 0.15 ml of each diluted test compound solution prepared above. To all the wells was added 0.15 ml of whole human blood, and the wells were incubated at 37° C. for 30 minutes. Lastly, to all the wells other than the Con A-unstimulated control wells, was added 0.03 ml of the above-prepared Con A solution, and all the wells were incubated at 37° C. for 48 hours. Low-speed centrifugation was conducted, and the supernatant in each well was collected and measured for IFN-γ concentration, by the use of a commercial ELISA kit. A test compound concentration of 50% production inhibition, i.e. $IC_{50}$ was determined. When the test compound was the compound of Example 2, the $IC_{50}$ was 5 μM.

Preparation Example 1

| | |
| --- | --- |
| Compound of Example 1 | 150 g |
| Avicel (trade name for microcrystalline cellulose, a product of Asahi Chemical Industry Co., Ltd.) | 40 g |
| Corn starch | 30 g |
| Magnesium stearate | 2 g |
| Hydroxypropylmethylcellulose | 10 g |
| Polyethylene glycol-6000 | 3 g |
| Castor oil | 40 g |
| Ethanol | 40 g |

The present active ingredient compound, Avicel, corn starch and magnesium stearate were mixed together and ground, and the mixture was shaped into tablets by using a conventional pounder (R 10 mm) for sugar coating. The tablets were coated with a film-coating agent consisting of hydroxypropylmethylcellulose, polyethylene glycol-6000, castor oil and ethanol, to prepare film-coated tablets.

Preparation Example 2

| | |
| --- | --- |
| Compound of Example 2 | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | A required amount |

The present active ingredient compound, citric acid, lactose, dicalcium phosphate, Pluronic F-68 and sodium lauryl sulfate were mixed together.

The mixture was sieved through a No. 60 screen. The sieved mixture was wet-granulated with an ethanol solution containing polyvinyl pyrrolidone, Carbowax 1500 and Carbowax 6000. When necessary, ethanol was added to convert the mixture into a paste-like mass. Corn starch was added, and mixing operation was conducted until uniform particles were formed. The particles were passed through a No. 10 screen, then placed in a tray, and dried in an oven at 100° C. for 12–14 hours. The dried particles were sieved through a No. 16 screen. Next, dry sodium lauryl sulfate and magnesium stearate were added to the sieved particles. The mixture was compressed into core tablets of desired shape by using a tablet machine.

The core tablets were treated with a varnish, and then talc was sprayed thereon for prevention of moisture absorption. On the surfaces of the resulting core tablets, an undercoat layer was formed. Varnish coating was made on the undercoat layer sufficient times so as to make the tablets suitable for internal use. Further, undercoat layer formation and smooth coating were conducted to make the coated tablets completely round and smooth. Color coating was conducted until the tablet surfaces came to have a desired color. After drying, the coated tablets were polished to obtain tablets of uniform gloss.

Preparation Example 3

| | |
|---|---|
| Compound of Example 2 | 5 g |
| Polyethylene glycol (mol. wt.: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

Parabens, sodium metabisulfite and sodium chloride were dissolved in distilled water of about half the above volume at 80° C. with stirring. The resulting solution was cooled to 40° C. In the solution were dissolved the present active ingredient compound, polyethylene glycol and polyoxyethylene sorbitan monooleate. To the resulting solution was added the remainder of distilled water to obtain a final volume. The thus-obtained solution was sterilized by passing through an appropriate filter paper, to prepare an injection.

What is claimed is:

1. A method for inhibiting production of TNF-α, IL-1β, IL-6 and INF-γ by administering to a patient in need thereof an agent for inhibiting production of TNF-α, IL-1β, IL-6 and INF-γ comprising, as the active ingredient, a thiazole compound or a pharmaceutically acceptable salt thereof of the formula:

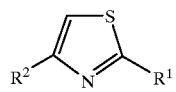

wherein $R^1$ is a phenyl group which may have one or more lower alkoxy groups as a substituent on the phenyl ring and $R^2$ is a pyridyl group which may have 1 to 3 carboxyl groups as a substituent on the pyridine ring.

2. The method of claim 1 wherein production of TNF-α, IL-1β, IL-6 and INF-γ is inhibited by inhibiting adhesion of neutrophils to vascular endothelial cells.

3. The method of claim 1 wherein the production of TNF-α is inhibited.

4. The method of claim 1, wherein the active ingredient is 6-[2-(3,4-diethoxyphenyl)thiazole-4-yl]pyridine-2-carboxylic acid.

5. The method of claim 2, wherein the active ingredient is 6-[2-(3,4-diethoxyphenyl) thiazole-4-yl]pyridine-2-carboxylic acid.

6. The method of claim 3, wherein the active ingredient is 6-[2-(3,4-diethoxyphenyl)thiazole-4-yl]pyridine-2-carboxylic acid.

7. A method for treating ARDS by administering to a patient in need thereof an agent for treating ARDS, comprising, as the active ingredient, a thiazole compound or a pharmaceutically acceptable salt thereof of the formula:

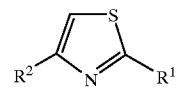

wherein $R^1$ is a phenyl group which may have one or more lower alkoxy groups as a substituent on the phenyl ring and $R^2$ is a pyridyl group which may have 1 to 3 carboxyl groups as a substituent on the pyridine ring.

8. The method of claim 7, wherein the active ingredient is 6-[2-(3,4-diethoxyphenyl)thiazole-4-yl]pyridine-2-carboxylic acid.

9. A method of treating asthma by administering to a patient in need thereof an agent for treating asthma comprising, as the active ingredient, a thiazole compound or a pharmaceutically acceptable salt thereof of the formula:

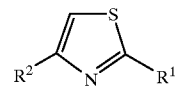

wherein $R^1$ is a phenyl group which may have one or more lower alkoxy groups as a substituent on the phenyl ring and $R^2$ is a pyridyl group which may have 1 to 3 carboxyl groups as a substituent on the pyridine ring.

10. The method of claim 9, wherein the active ingredient is 6-[2-(3,4-diethoxyphenyl)thiazole-4-yl]pyridine-2-carboxylic acid.

11. A method of treating Crohn disease by administering to a patient in need thereof an agent for treating Crohn disease, comprising as the active ingredient, a thiazole compound or a pharmaceutically acceptable salt thereof of the formula:

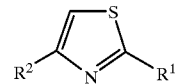

wherein $R^1$ is a phenyl group which may have one or more lower alkoxy groups as a substituent on the phenyl ring and $R^2$ is a pyridyl group which may have 1 to 3 carboxyl groups as a substituent on the pyridine ring.

12. The method of claim 11, wherein the active ingredient is 6-[2-(3,4-diethoxyphenyl)thiazole-4-yl]pyridine-2-carboxylic acid.

* * * * *